United States Patent [19]

Block

[11] 4,341,110
[45] Jul. 27, 1982

[54] PERCOLATION TESTING METHOD AND APPARATUS

[76] Inventor: Philip M. Block, 58 Fleetwood Rd., Newington, Conn. 06111

[21] Appl. No.: 161,139

[22] Filed: Jun. 19, 1980

[51] Int. Cl.³ .............................................. G01N 15/08
[52] U.S. Cl. ........................................... 73/38; 73/73; 73/312
[58] Field of Search ............................... 73/73, 312, 38

[56] References Cited

U.S. PATENT DOCUMENTS

| | | | |
|---|---|---|---|
| 1,054,849 | 3/1913 | Lawrence | 73/312 |
| 1,494,561 | 5/1924 | Nielsen | 73/312 |
| 2,716,341 | 8/1955 | Ilfrey | 73/312 |
| 3,162,044 | 12/1964 | Lee | 73/312 |
| 3,427,632 | 2/1969 | Vahs et al. | 73/312 |
| 3,892,126 | 7/1975 | Curtin | 73/38 |
| 4,099,406 | 7/1978 | Fulkerson | 73/73 |
| 4,182,157 | 1/1980 | Fink | 73/73 |

Primary Examiner—Donald O. Woodiel
Attorney, Agent, or Firm—Fishman & Van Kirk

[57] ABSTRACT

Apparatus for automatically recording the rate of fluid absorption of the soil includes three subsystems which may be easily assembled on site. During a test procedure the rate of descent of a float is recorded on a tape by a timer controlled marker.

4 Claims, 4 Drawing Figures

PERCOLATION TESTING METHOD AND APPARATUS

BACKGROUND OF THE INVENTION

1. Field of the Invention

The present invention relates to testing the fluid absorption rate of soil. More particularly, the present invention is directed to soil testing apparatus and particularly to apparatus which while unattended will provide a permanent record of the rate of absorption of fluid by soil or the rate of fluid infiltration into a bore hole. Accordingly, the general objects of the present invention are to provide novel and improved methods and apparatus of such character.

2. Description of the Prior Art

The water absorption or percolation characteristics of soil are of critical importance in determining whether a proposed land use is appropriate. Thus, by way of example only, one of the primary responsibilities of field environmental health workers is evaluation of individual sewage disposal system sites. This evaluation commonly includes a "percolation test" which provides a measure of the soil's ability to absorb liquid run-off from a septic tank. Thus, the results of the percolation test will determine the square footage of absorptive soil necessary to handle a given output from a home or business.

At present, in order to perform a soil percolation test, an evacuation of a given diameter is made down to the level at which the contemplated absorption is to occur. That excavation is filled with water and, after a certain amount of time has passed for some level of equilibrium or saturation to have occurred, the hole is refilled and a mark placed at a high water point. This is usually accomplished by either placing a cross bar with hanging member above the hole or by inserting a marker in the side wall of the hole. The time when the cross bar or marker is put in place is recorded. Thereafter, using preset periods of time, a series of measurements of the water level in the hole are taken and manually recorded. A conventional, manual percolation test of the type being described requires the presence of an observer for periods of up to two hours. Further, the information of interest is obtained by making a comparison between two separated points; i.e., the water level at the time the measurement is taken and either the previous or the initial level where the marker was placed; and these points are customarily a significant distance below the surface level and thus must be viewed at a substantial angle. This problem of looking at two points at the same time combined with the extreme perspective makes accurate measurements difficult. The necessity of making the measurements at set uniform time intervals further contributes to the inaccuracy of the prior art testing procedure since distractions, conversation, boredom, etc. often result in the time intervals between successive measurements varying. From a purely economic viewpoint, of course, the requirement that an individual spend up to two hours doing so little; i.e., making a few measurements as the water is absorbed into the soil; is highly inefficient. Attempts to enhance efficiency, and thereby reduce costs of an individual test, by assigning the test personnel to other tasks between the successive measurements only contributes to the inaccuracies of the measurement. Thus, in order to record the soil percolation characteristics with the required accuracy, the test site needs continual supervision.

Apparatus for use in performing soil percolation tests is well known in the art. Examples of such prior art apparatus are found in U.S. Pat. Nos. 3,926,143, 3,945,247, 4,099,406 and 4,182,157. The prior art soil percolation testers, while they avoid the need for manually placing markers in the excavation and making comparative measurements down in the hole, are nevertheless plagued by one or more inherent deficiencies. The most common of these deficiencies is the requirement for continual operator supervision if the desired information is to be accurately recorded. A further common deficiency resides in the relative complexity of the devices which often contributes to set-up problems and/or transportation difficulties. An additional deficiency, incident to the comparatively harsh treatment to which such apparatus is often subjected, results from a lack of modular construction which prevents damaged or consumed components from being discarded and replaced by new components.

SUMMARY OF THE INVENTION

The present invention overcomes the above-discussed and other disadvantages and deficiencies of the prior art by providing a novel and improved soil percolation tester and a testing procedure which utilizes this novel test apparatus. The present invention thus permits the fluid absorption rate of soil to be measured with greater accuracy than has heretofor been possible and this enhanced accuracy is achieved without the need for continual supervision.

Apparatus in accordance with a preferred embodiment of the present invention includes a perforated housing designed to be positioned in and supported from the bottom of the customary excavation. The apparatus of the preferred embodiment further includes a float, having a vertical rod extending therefrom, which is sized and shaped to move freely within the housing. The upper portion of the vertical rod extending from the float is formed into a generally C-shaped channel sized and shaped to receive a replaceable recording medium. A battery powered clock and marker mechanism also forms part of the present invention. The casing of this clock-marker mechanism is received in the housing at the upper end thereof. The casing is removably supported on the upper edge of the pipe and includes a guide slot which receives the channel-shaped extension of the float rod. Accordingly, as the float descends within the housing a recording medium mounted in the channel will move relative to the output mechanism of the clock-marker subassembly. When a test is initiated the recording medium will be periodically marked, under control of the clock, and an accurate and permanent record of the test results will be provided.

A particularly unique feature of a percolation tester in accordance with the present invention is that the three principal components; i.e., the housing, the float and rod assembly and the clock-marker assembly; need not be assembled using mechanical fasteners and thus the entire apparatus may be easily broken down for movement from site to site or storage and individual components may be readily replaced if lost or damaged. Further, as noted above, apparatus in accordance with the present invention provides an accurate permanent record which may be easily stored for future reference. This may be contrasted with the prior art practice of producing hand-written records on papers of various size and shape.

BRIEF DESCRIPTION OF THE DRAWING

The present invention may be better understood and its numerous objects and advantages will become apparent to those skilled in the art by reference to the accompanying drawing wherein like reference numerals refer to like elements in the several FIGURES and in which.

DESCRIPTION OF THE PREFERRED EMBODIMENT

Figure 1:
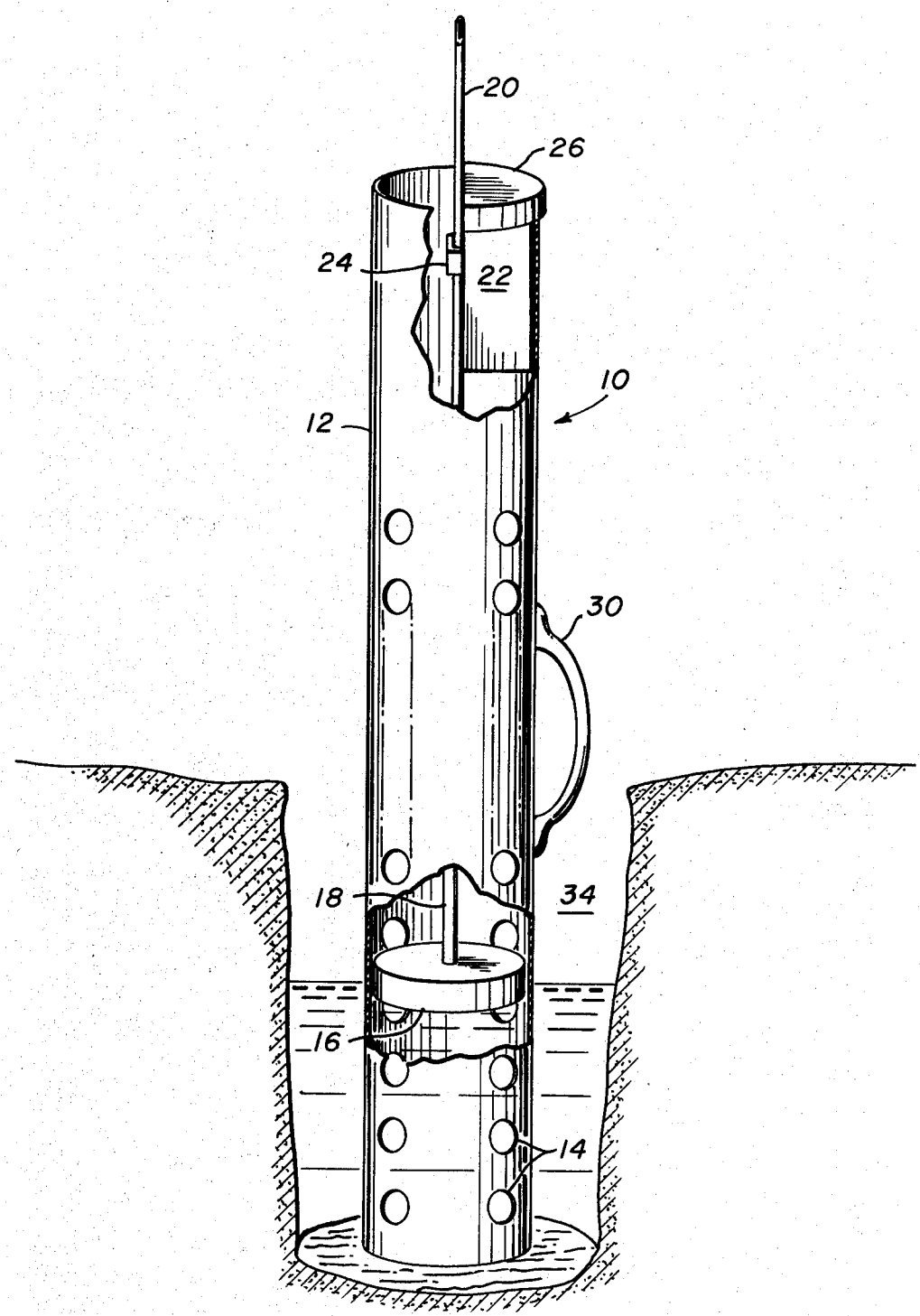
FIG. 1 is a side elevation view, partly in section, of soil percolation testing apparatus in accordance with a preferred embodiment of the present invention.

With reference now to the drawing, a soil percolation tester in accordance with a preferred embodiment of the present invention is indicated generally at 10. The test apparatus 10 includes three principal components or subsystems. The first of these components is the tubular housing or pipe 12 which, at least at its lower end, is provided with a plurality of perforations 14. The second component comprises the float subassembly 30 which includes the actual float member 16, the float rod 18 and the channel-shaped float rod extension 20. The third component of percolation test apparatus in accordance with the present invention consists of a clock-marker subassembly which is indicated generally at 22.

The clock-marker subassembly will include a guide member 24 for the channel extension 20 of float rod 18. The clock-marker subassembly 22, as may best be seen from FIG. 4, also includes a cap member 26 of generally semi-circular shape and of slightly larger diameter than tube 12. The cap 26 is provided with a downwardly extending flange 28 (FIG. 4) about the arcuate portion of its periphery and the inner diameter of flange 28 is substantially identical to the outer diameter of tube 12. Accordingly, as may be seen from the drawing, the subassembly 22 is merely supported in the upper end of tube 12 from the top edge thereof. Thus, for assembly and disassembly, the guide 24 will merely be slipped over the channel-shaped float rod extension 20, the tube placed in tube 12 and the subassembly 22 slid downwardly until the flange 28 engages the top outer surface of the tube. If deemed necessary or desirable, the tube 12 may be provided with a carrying handle 30; the tube typically being thirty inches in length.

Figure 4:
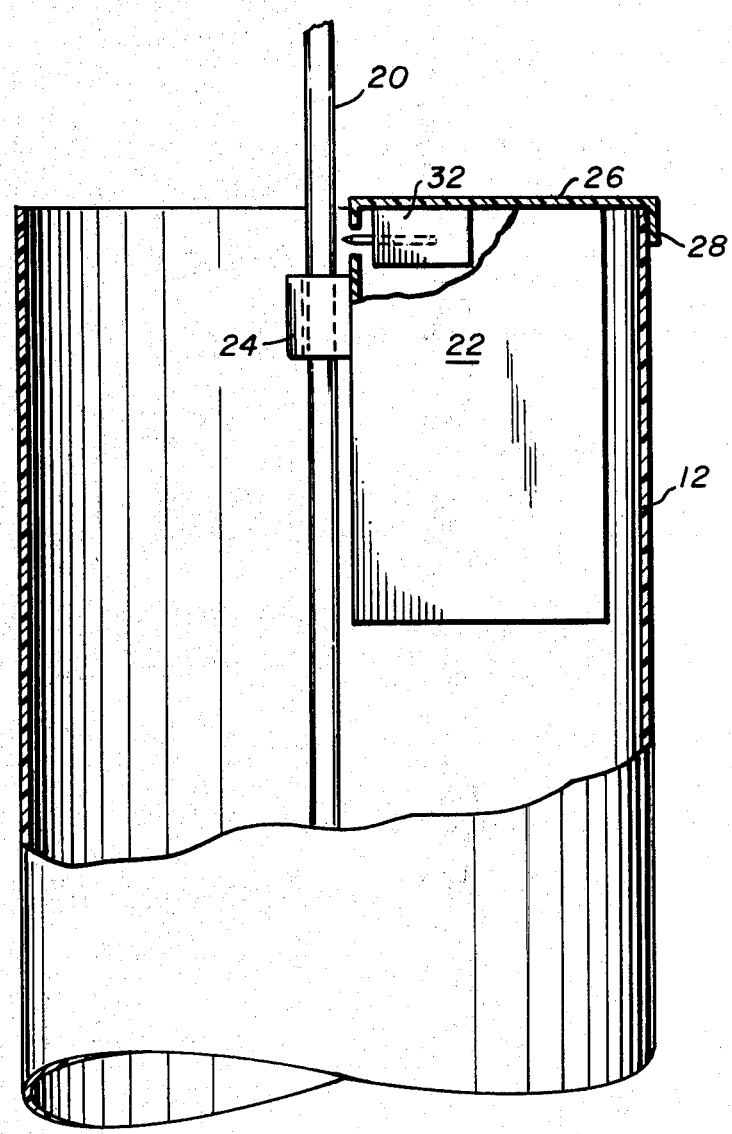
FIG. 4 is an enlarged side elevation view, partly in section, depicting the clock-marker subassembly of the apparatus of FIG. 1.

The timer-marker subassembly 22 will comprise a power source, typically a conventional 9 volt battery, a timing circuit and a solenoid controlled marker 32 (FIG. 4). The marker 32 will typically comprise a pen but may also comprise a punch, spark gap or other suitable marking instrumentality. The timing circuit, which will be comprised of integrated circuitry, will include a clock, counter and switch. The switch will be connected in series between the current source and solenoid and will, under control of the counter, be periodically closed to thereby deliver current to the solenoid thus causing the marker to move into contact with a printed paper tape which has been inserted in the channel extension 20 of float rod 18. The paper tape will be graduated, typically in fractions of inches, and the marker will typically be energized every five minutes. The only operational control will constitute a manually operated switch, not shown, which connects the battery to the electronics.

In operation, the hole 34 will be dug to the requisite depth, the test apparatus assembled in the manner described above, and tube 12 positioned in the hole with its axis oriented substantially vertically. The soil will be presoaked, as described above in the discussion of prior art procedures, the paper tape will thereafter be inserted in channel 20 and the hole 34 refilled with water to the prescribed depth. The apparatus will then be turned on resulting in an initial immediate marking of the paper tape. The operator may then leave the site and/or perform other duties. Upon returning to the site, the operator need only turn off the power and remove the paper tape which will provide an accurate measurement of the rate of water absorption into the soil. Once the tape has been removed, the apparatus may be broken down into its three principal components for storage or for movement to a new test site.

Figure 2:
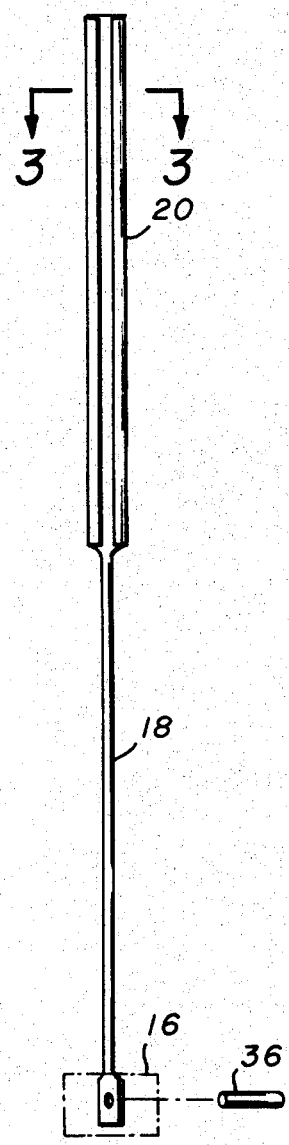
FIG. 2 is a front view of the float-rod subassembly of the apparatus of FIG. 1.
Figure 3:
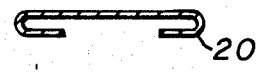
FIG. 3 is a view taken along the line 3—3 of FIG. 2.

In accordance with one reduction in practice of the present invention, the tube 12 was formed from a four inch diameter piece of PVC pipe and was 30 inches in length. The float 16 may be comprised of polystyrene and may be pinned to rod 18 by means of a pin 36 as indicated in FIG. 2. The timer-marker subassembly 22 will be completely encapsulated in an epoxy resin and thus will be waterproofed, durable, and maintenance free. Of course, during encapsulation, protective measures are taken to ensure that there will be no interference with free movement of the solenoid operated pen or other marker. The potted subassembly will be made integral with cap 26 by any suitable means. It will be understood that the cap 26 may be of circular shape and thereby define a second guide means for the channel extension 20 of rod 18.

While a preferred embodiment has been shown and described, various modifications and substitutions may be made thereto without departing from the spirit and scope of the invention. Accordingly, it will be understood that the present invention has been described by way of illustration and not limitation.

What is claimed is:

1. Apparatus for measuring the rate of change of the level of fluid in an excavation in a porous medium comprising:

a perforated tubular housing having an axis;

float means positioned for axial movement within said tubular housing;

elongated rod means, said rod means being affixed at a first end to said float means, said rod means having a recording medium receiving portion adjacent a second end thereof; and recording means, said recording means being removably supported within said housing at a first end thereof, said recording means including timer means and means controlled by signals produced by said timer means for periodically marking the recording medium, said recording means further including guide means for said rod means second end whereby the recording medium is juxtapositioned to said recording means marking means, the points at which the recording medium is marked by said marking means being a function of the position of said float means in said housing and said timer means output signals.

2. The apparatus of claim 1 wherein said housing has a cylindrical shape and wherein at least a first portion of said recording means has a diameter which is greater than the outer diameter of said housing means, said first portion of said recording means defining a rim which engages the outer surface of said housing means to support said recording means in said housing means.

3. The apparatus of claim 1 wherein said rod means recording medium receiving portion comprises a generally C-shaped channel extending inwardly from the second end of said rod means, said channel having a flat bottom and a pair of facing edge portions which define an opening through which the marking means operates.

4. The apparatus of claim 3 wherein said housing has a cylindrical shape and wherein at least a first portion of said recording means has a diameter which is greater than the outer diameter of said housing means, said first portion of said recording means defining a rim which engages the outer surface of said housing means to support said recording means in said housing means.

* * * * *